(12) United States Patent
Vergoullis et al.

(10) Patent No.: US 10,420,632 B2
(45) Date of Patent: Sep. 24, 2019

(54) DENTAL TOOLS SYSTEM AND METHOD

(71) Applicant: VP INNOVATO HOLDINGS LTD., Lemessos (CY)

(72) Inventors: Ioannis Vergoullis, Rhodes (GR); Georgios Papadopoulos, Rhodes (GR)

(73) Assignee: VP INNOVATO HOLDINGS LTD., Lemessos (CY)

( * ) Notice: Subject to any disclaimer, the term of this patent is extended or adjusted under 35 U.S.C. 154(b) by 0 days.

(21) Appl. No.: 16/311,651

(22) PCT Filed: Jun. 9, 2017

(86) PCT No.: PCT/IB2017/053419
§ 371 (c)(1),
(2) Date: Dec. 19, 2018

(87) PCT Pub. No.: WO2017/221097
PCT Pub. Date: Dec. 28, 2017

(65) Prior Publication Data
US 2019/0201167 A1    Jul. 4, 2019

(30) Foreign Application Priority Data

Jun. 24, 2016 (GR) .............................. 20160100338
Oct. 17, 2016 (GR) .............................. 20160100536

(51) Int. Cl.
*A61C 8/00* (2006.01)
*A61C 1/08* (2006.01)
(Continued)

(52) U.S. Cl.
CPC .............. *A61C 8/009* (2013.01); *A61C 1/084* (2013.01); *A61C 3/04* (2013.01); *A61C 8/0001* (2013.01);
(Continued)

(58) Field of Classification Search
CPC .......... A61C 8/0001; A61C 8/009; A61C 3/04
See application file for complete search history.

(56) References Cited

U.S. PATENT DOCUMENTS

| 512,840 A | 1/1894 | Phelps |
| 5,180,303 A | 1/1993 | Hornburg et al. |

(Continued)

FOREIGN PATENT DOCUMENTS

| EP | 2343025 A2 | 7/2011 |
| GB | 2502328 A | 11/2013 |

(Continued)

OTHER PUBLICATIONS

Albrektsson et al. "Osseointegrated dental implants" Dent. Clin. North Am.; Jan. 1986; 30(1); pp. 151-174.
(Continued)

*Primary Examiner* — Ralph A Lewis
(74) *Attorney, Agent, or Firm* — Steinfl + Bruno LLP

(57) ABSTRACT

A dental tools system with a plurality of guide tabs; a mold and a plurality of tissue punch heads. The mold has a plurality of mold holes, each mold hole having a top portion and a bottom portion. Each guide tab fits in the top portion of one of the mold holes and each tissue punch head fits in the top portion of one of the mold holes. A method of placing dental implants is also described.

19 Claims, 13 Drawing Sheets

(51) Int. Cl.
*A61C 3/04* (2006.01)
*A61C 9/00* (2006.01)
*A61C 13/00* (2006.01)

(52) U.S. Cl.
CPC ............ *A61C 8/008* (2013.01); *A61C 8/0089* (2013.01); *A61C 9/004* (2013.01); *A61C 13/0004* (2013.01); *A61C 2008/0084* (2013.01)

(56) References Cited

U.S. PATENT DOCUMENTS

| | | | |
|---|---|---|---|
| 5,183,053 | A | 2/1993 | Yeh et al. |
| 5,759,036 | A | 6/1998 | Hinds |
| 5,846,079 | A | 12/1998 | Knode |
| 6,672,871 | B2 | 1/2004 | Hurson |
| 7,922,488 | B2 | 4/2011 | Falk et al. |
| 8,628,327 | B1 | 1/2014 | Blaisdell et al. |
| 9,572,640 | B2 | 2/2017 | Blaisdell et al. |
| 9,895,209 | B2 | 2/2018 | Blaisdell et al. |
| 10,136,974 | B2 | 11/2018 | Vergoullis et al. |
| 2002/0106610 | A1 | 8/2002 | Hurson |
| 2003/0211445 | A1 | 11/2003 | Klardie et al. |
| 2008/0176186 | A1 | 7/2008 | Schaub et al. |
| 2010/0105009 | A1 | 4/2010 | Karkar et al. |
| 2010/0196849 | A1 | 8/2010 | Moneim et al. |
| 2011/0129798 | A1 | 6/2011 | Zucker et al. |
| 2011/0200968 | A1 | 8/2011 | Laizure, Jr. |
| 2012/0295223 | A1 | 11/2012 | Robb et al. |
| 2013/0177872 | A1 | 7/2013 | Blaisdell et al. |
| 2014/0080095 | A1 | 3/2014 | Suttin et al. |
| 2014/0100327 | A1 | 4/2014 | Yamaguchi et al. |
| 2014/0100642 | A1 | 4/2014 | Mashiach, II |
| 2014/0124969 | A1 | 5/2014 | Blaisdell et al. |
| 2014/0193775 | A1 | 7/2014 | Hogan et al. |
| 2014/0319713 | A1 | 10/2014 | Blaisdell et al. |
| 2015/0100090 | A1 | 4/2015 | Burke |
| 2015/0351877 | A1 | 12/2015 | Boehm et al. |
| 2017/0007372 | A1 | 1/2017 | Blaisdell et al. |
| 2017/0128176 | A1* | 5/2017 | Vergoullis ............ A61C 8/0001 |
| 2019/0029786 | A1* | 1/2019 | Vergoullis ............ A61C 19/003 |

FOREIGN PATENT DOCUMENTS

| | | |
|---|---|---|
| JP | H08196549 A | 8/1996 |
| KR | 20100048968 A | 5/2010 |
| WO | 2015/189647 A1 | 12/2015 |
| WO | 2015/189648 A2 | 12/2015 |

OTHER PUBLICATIONS

Boynuegri et al. "Effect of different localizations of microgap on clinical parameters and inflammatory cytokines in peri-implant crevicular fluid: A prospective comparative study" Clinical Oral Investigations; 2012; 16 (2):pp. 353-361.

Chu et al. "The dual-zone therapeutic concept of managing immediate implant placement and provisional restoration in anterior extraction sockets" Compendium of Continuing Education in Dentistry; Aug. 2012; vol. 33, No. 7; pp. 524-534.

Chu et al. "Managing esthetic challenges with anterior implants. Part 1: midfacial recession defects from etiology to resolution" Compendium of Continuing Education in Dentistry; Oct. 2013; vol. 34, Special Issue 7; pp. 26-31.

International Preliminary Report on Patentability for PCT Application No. PCT/GR2015/000029, filed on Jun. 12, 2015, on behalf of Vergoullis, Ioannis, dated Dec. 6, 2016. 66 pgs.

International Search Report for International Application No. PCT/GR2015/000029, filed on Jun. 12, 2015, on behalf of Vergoullis, Ioannis, dated Sep. 29, 2015. 3 pgs.

Non-Final Office Action for U.S. Appl. No. 15/318,085, filed Dec. 12, 2016, on behalf of Ioannis Vergoullis, dated Apr. 18, 2018. 17 pgs.

Notice of Allowance for U.S. Appl. No. 15/318,085, filed Dec. 12, 2016, on behalf of GP Innovato Cyprus LTD, Limassol, Cyprus, dated Aug. 27, 2018. 5 pgs.

Written Opinion for International Application No. PCT/GR2015/000029, filed Jun. 12, 2015, on behalf of Ioannis Gergoullis, dated Sep. 29, 2015. 5 pgs.

International Preliminary Report on Patentability for PCT Application No. PCT/IB2017/053419, filed on Jun. 9, 2017, on behalf of VP Innovato Holdings Ltr. dated Sep. 6, 2018. 20 pgs.

International Search Report for PCT Application No. PCT/IB2017/053419, filed on Jun. 9, 2017, on behalf of VP Innovato Holdings Ltr. dated Aug. 17, 2017. 5 pgs.

Written Opinion for PCT Application No. PCT/IB2017/053419, filed on Jun. 9, 2017, on behalf of VP Innovato Holdings Ltr. dated Aug. 17, 2017. 9 pgs.

\* cited by examiner

DENTAL TOOLS SYSTEM AND METHOD

CROSS REFERENCE TO RELATED APPLICATIONS

The present application is the U.S. national stage of International Patent Application PCT/IB2017/053419 filed internationally on Jun. 9, 2017, which, in turn, claims priority to Greek Patent Application No. 20160100338 filed on Jun. 24, 2016 and to Greek Patent Application No. 20160100536 filed on Oct. 17, 2016, all of which are incorporated by reference herein in their entirety, including any drawings.

TECHNICAL FIELD

This invention belongs to the field of tools used by dentists for operating in dental tissue, in order to manage the soft tissue around implants or similar operations.

STATE OF THE ART

Implant placement involves some operations, related to the manufacturing and handling of healing abutments and impression posts.

Dentists must try to adjust to the patient's edentulous space the maximum possible. Computed aided design is mostly used, but it is more expensive and requires a hardware pack which is not always available in every part of the world.

A more traditional approach would include several stages of measuring and molding in the patient's mouth, which is quite unpleasant, both for the patient himself and for the dentist.

It would be desirable to find some tools suitable for managing this process without requiring a computer machine and without making the process excessively laborious.

DESCRIPTION OF THE INVENTION

The invention provides an alternative solution for this problem by means of a dental tools system in accordance with the present disclosure. Preferred embodiments are also disclosed.

In a first inventive aspect, the invention provides a dental tools system, comprising
  a plurality of guide tabs;
  a mold comprising a plurality of mold holes, each mold hole comprising a top portion and a bottom portion; and
  a plurality of tissue punch heads;
wherein
  each guide tab fits in the top portion of one of the mold holes; and
  each tissue punch head fits in the top portion of one of the mold holes.

This system comprises elements which are interrelated. The dentist finds it easier to perform the operations related to the placement of an implant in a patient with a dental tools system according to the invention, since the system provides standard sizes and shapes for every step and for every dental piece.

The fact that guide tabs and tissue punch heads fit in the top portion of one of the mold holes should be understood as a person skilled in the art would; i.e., as that at least part of a top portion of the mold holes has a shape such that when a guide tab or a tissue punch head is placed in this top portion, it reaches a position with stable equilibrium, where it has a very small tolerance to move, and may only be extracted by the same way as it was placed in the top portion.

In some particular embodiments, the dental tools system further comprises a plurality of first tubes and a plurality of second tubes, wherein each first tube fits in the top portion of one of the mold holes, and each second tube fits in a first tube, and comprises a central through hole.

This system is even more complete, and allow the dentist the use of first and second tubes, which are useful for more exactly positioning the tissue punch heads. The second tubes allow the positioning of a drilling tool inside the first tube.

In some particular embodiments, there are at least three different shapes of guide tabs, mold holes and tissue punch heads, each shape with at least three different sizes, each shape having a cross section which comprises at least one straight portion and one curved portion.

These types of cross sections adapt to the dental pieces in a very good way. Triangles with round edges, squares with round edges and rectangles with round edges are examples of shapes which may adapt to incisors, canines, premolars and molars.

In some particular embodiments, at least one guide tab comprises a first lateral coupling recess and a second lateral coupling recess.

Lateral coupling recesses are useful to attach guide tabs to other elements, which may be inserted in these recesses.

In some particular embodiments, the second lateral coupling recess of the guide tab is greater than the first lateral coupling recess.

Differences in the size of the coupling recesses allow the insertion of different types of handles.

In some particular embodiments, the dental tools system further comprising a handle comprising first magnetic means and wherein the first and second lateral coupling recesses of the guide tab are substantially of the same shape, and wherein the first and/or second lateral coupling recesses comprise second magnetic means, adapted to interact with the first magnetic means.

Magnetic means allow the attachment of different types of handles to the guide tabs. In some embodiments, first magnetic means comprise a magnet, and second magnetic means comprise a ferromagnetic material. In other embodiments, first magnetic means comprise a ferromagnetic material, and second magnetic means comprise a magnet.

In some particular embodiments, at least one guide tab comprises a central bore, suitable for letting a drilling tool pass through the guide tab.

This central bore is very useful, since guides the dentist to perform any drilling operation with the reference provided by the guide tab itself, since this guide tab corresponds with a mold hole intended to be used to create the healing abutment and impression post that would be used in the complete operation.

In some embodiments, at least one guide tab comprises orientation marks, which are parallel and are suitable for helping the positioning of further dental tools.

These orientation marks are useful for the dentist to correctly orientate the prosthetic connection of the healing abutment and impression post.

In some embodiments, the guide tabs are not physical, but virtual, as they are included in a database contained in a scanner. The scanner is applied in the patient's edentulous space and a virtual guide tab is selected. Accordingly, the corresponding mold hole, tissue punch head and tubes may be chosen.

In some embodiments, the virtual guide tabs are used as a part of a software, in order to evaluate the edentulous space of a patient, so that the proper virtual guide tab may be selected. Afterwards, the corresponding mold hole and/or tissue punch head, and/or tubes are selected and manufactured through 3D printing and/or milling.

In some embodiments, the virtual guide tabs are used as a part of a software in order to evaluate the edentulous space of a patient, so that the proper virtual guide tab or tabs may be selected. Accordingly, the negative replication of the corresponding mold hole or holes are selected and manufactured through 3D printing and/or milling.

In some embodiments, the mold comprises
- a mold base, which comprises the bottom portions of the holes;
- a mold superstructure, which comprises the top portions of the mold holes, each top portion having a cross section which decreases while advancing towards the mold base;
- wherein the mold base and the mold superstructure may be engaged in more than one operation position so that some top portions match with bottom portions in each operation position.

This way of arranging the mold holes allows the dentist exchange the mold base with different mold superstructures, or vice versa.

In some embodiments, the mold base comprises first positioning means and the mold superstructure comprises second positioning means suitable for interacting with the first positioning means in a stable position to keep constant the relative position of the mold base and the mold superstructure.

These positioning means provide the mold with better stability against unintentional movements or hits which may be caused by the dentist.

In some embodiments, the first positioning means and the second positioning means have more than one stable position.

This feature makes the mold able to have at least twice as possible combinations of top and bottom portions.

In some embodiments, the mold superstructure comprises a first frame and a first insert, the first insert comprising the top portions of the mold holes and being inserted inside the first frame. Further, the mold base comprises a second frame and a second insert, the second insert comprising the bottom portions of the mold holes and being inserted inside the second frame.

The first and second inserts are usually made of silicone, which is easy to manufacture and to process. However, this does not exclude the possibility for the inserts to be made out of metallic, plastic, ceramic or other suitable material. The first and second frame provide solid covers so that the interactions between the superstructure and the base are performed by the frames. Each set of frame and insert may be made of the same material or of different materials.

In some embodiments, the mold superstructure also comprises a first frame and a first insert, the first insert comprising the top portions of the mold holes and being inserted inside the first frame. But in these embodiments, the mold base comprises a second frame with insert holes, each insert hole comprising a seat, and also comprises a plurality of individual fitting inserts, each one of these individual fitting inserts being adapted to fit in at least one of the insert holes of the second frame. Each individual fitting insert comprises a body, which in turn comprises one of the bottom portions, and a wing, adapted to fit in the seat of one of the insert holes. The shape of the seat prevents the individual fitting insert from rotating once the individual fitting insert is fitted into the seat.

Advantageously, the individual fitting inserts may be replaced without replacing more elements of the dental tools system, and the wing, being adapted to fit in a seat, provides anti-rotational properties to these individual fitting inserts. This may be achieved, for example, providing a seat which does not have circular symmetry, so that the wing fits the seat in a single position. Other ways, such as magnets, may also be within the scope of the invention. Further, an easy, secure, reproducible and reversible positioning and orienting of the individual fitting insert is achieved, so that the individual insert is reliably used during the operation of the tools system and may be easily replaced when necessary.

In some particular embodiments, each individual fitting insert is secured to the second frame by means of a retention screw.

This retention screw may fit in a lower threaded portion of the individual fitting insert, to secure the individual fitting insert to the second frame in a detachable way, the individual fitting insert being thus replaceable.

In some particular embodiments, the wing of at least one individual fitting insert comprises one shoulder cavity, adapted to receive at least part of the prosthetic connection and/or a shoulder of a healing abutment.

These individual fitting inserts provide a way of securing the healing abutment to the bottom portion of the mold holes, without allowing said healing abutment to rotate or displace uncontrolledly in the mold hole. Since the individual fitting inserts are replaceable, different individual fitting inserts may be provided with different shoulder cavities, thus adapting to future designs.

In some particular embodiments, the second positioning means are located in the frame of the mold superstructure; one of the first and second positioning means comprises a concavity; and the other of the first and second positioning means comprises at least one of a ball with spring, a convexity or a plate.

There are many ways so that the superstructure and the base may be coupled in different stable positions, so that one top portion may fit with several bottom portions, and vice versa. One of the ways is that one of the first and second positioning means comprise a concavity. This concavity is suitable for a convexity to fit in, so that a stable coupling is achieved. This convexity may be a simple convexity or a ball, with or without a spring, or a plate, which may fit in several concavities comprised in a roulette.

However, these embodiments allow the possibility of properly align all the top and bottom portions of holes, thus maximizing the possible combinations, since all the top portions, comprised in the mold superstructure, may be faced with each of the bottom portions, comprised in the base.

In some embodiments, some bottom portions are oriented in a different direction from some top portions.

This feature makes the mold able to manufacture healing abutments and impression posts which may have their prosthetic connections oriented in different directions with respect to their custom bodies.

In these embodiments, each bottom portion is extended along a bottom straight direction, which is perpendicular to all the cross sections of said bottom portion. Each top portion is in turn extended along a top straight direction, which is perpendicular to all the cross sections of said top portion. In some embodiments, the top straight direction of a top portion and the bottom straight direction of the corresponding bottom portion are not the same. In some embodiments, these directions may form between 1 and 45 degrees with respect to each other.

The bottom portions have a cross section which varies in size and/or shape while advancing towards the mold superstructure, but all cross sections are oriented according to parallel planes, which are perpendicular to the straight direction of the bottom portion. Some of the bottom portions have a cross section which comprises a straight portion and a curved portion. In particular embodiments, these cross sections are triangular, or polygonal or rectangular, or square, with or without round edges.

In some embodiments, the top portions have an inferior zone with a cross section which varies in size and/or shape in the direction towards the mold base, in such a way that the shape of the inferior zone of the top portion is different from the shape of the rest of the top portion.

This feature makes the holes produce a wider range of different healing abutments and impression posts, which may adapt to different shapes and angulations which are present in the patient's mouths.

In some embodiments, some of the top portions have at least one cross section which comprises a straight portion and a curved portion.

This feature allows the use of abutments comprising different shoulders, also with the same shape of the custom bodies of the abutments and impression posts.

In some embodiments, the top portions have a regular surface, as that which may be expressed by a polynomic, exponential or logarithmic mathematical formula, or a combination thereof, with a mean roughness Ra lower than 10 µm.

This embodiment makes that the abutments and impression posts produced by the molds have a regular and smooth surface, which is more favorable for the patient's gingival emergence profile and allow better hard and soft tissue adaptation.

In some embodiments, the dental tools system further comprises detachable inserts suitable for modifying the final profile of some top and/or bottom portions.

This feature provides a different way of obtaining different profiles from the mold holes. A real dental piece and/or a temporary prosthesis may be introduced in a standard mold hole, and then the spaces between the dental piece and the hole being filled with these detachable inserts. When the dental piece is removed, a hole with the exact negative replication of this dental piece is formed in the mold hole. These detachable inserts in cases inserted in the bottom hole, once coupled to the latter they alter the profile/shape of the bottom hole allowing the coupling of abutment and impression post cores with different profile/shape prosthetic connections to the same bottom hole.

In a second inventive aspect, the invention provides a method of placing dental implants in an edentulous space using a dental tools system according to any of preceding claims, the method comprising the steps of
choose a guide tab which characterizes an edentulous space in size and shape;
use a mold hole which corresponds with this guide tab to manufacture a healing abutment and/or an impression post;
use this healing abutment and/or impression post as a reference for placing a dental implant in the edentulous space.

This way of choosing the suitable elements for the implant placement operations is much faster and simpler than any method using the state of the art systems.

In a particular embodiment, this method further comprises at least one of these further steps
use a tissue punch head which corresponds with this guide tab to cut the soft tissue; and/or
use this healing abutment and/or impression post for filling and supporting and recording the space created by the tissue punch head of the soft tissue around a dental implant placed in the edentulous space.

BRIEF DESCRIPTION OF THE DRAWINGS

To complete the description and in order to provide for a better understanding of the invention, a set of drawings is provided. Said drawings form an integral part of the description and illustrate an embodiment of the invention, which should not be interpreted as restricting the scope of the invention, but just as an example of how the invention can be carried out. The drawings comprise the following figures.

DETAILED DESCRIPTION OF THE INVENTION

Figure 1:
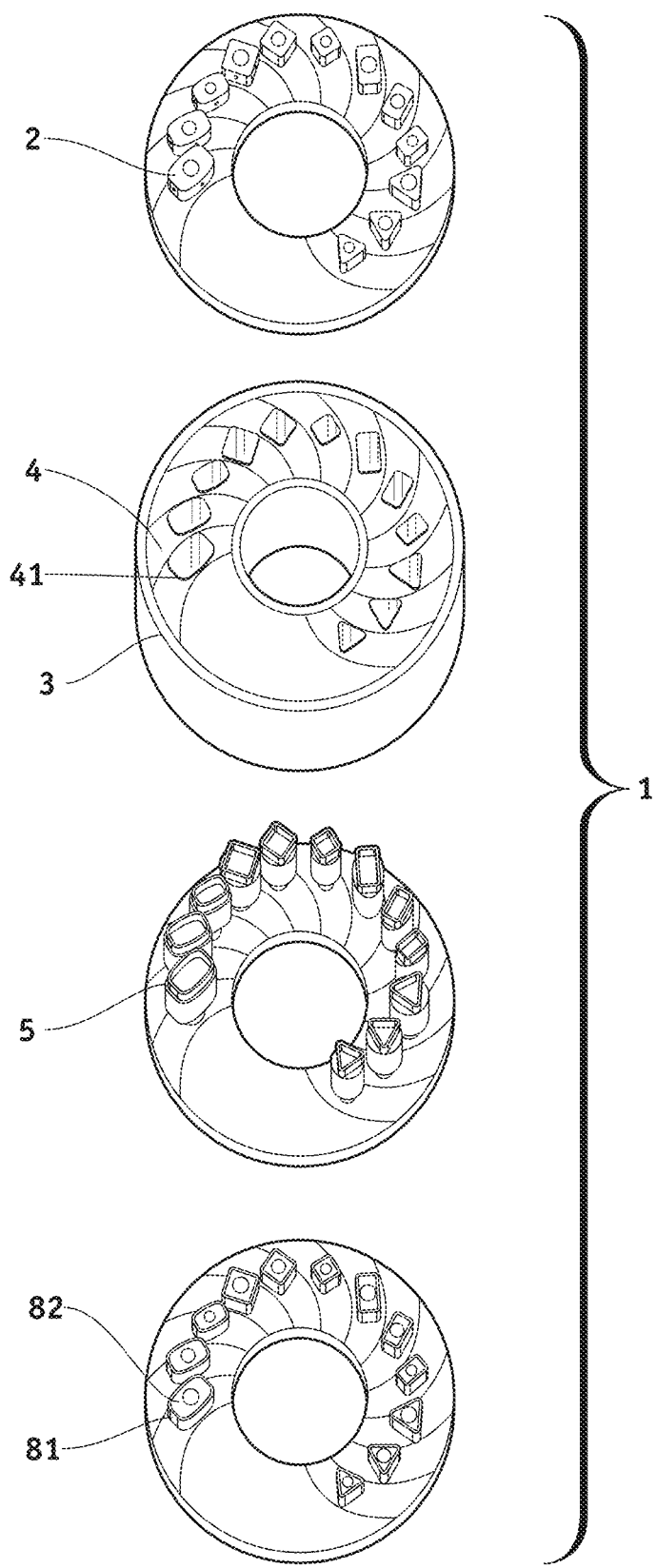
FIG. 1 shows a particular embodiment of dental tools system according to the invention.

FIG. 1 shows a dental tools system 1 comprising
a plurality of guide tabs 2;
a mold 3 comprising a plurality of mold holes 4, each mold hole comprising a top portion 41 and a bottom portion not shown in this figure;
a plurality of tissue punch heads 5; and
a plurality of first tubes 81 and second tubes 82.

Each guide tab 2 fits in the top portion 41 of one of the mold holes 4; and each tissue punch head 5 fits in the top portion 41 of one of the mold holes 4. Each first tube 81 fits in the top portion 41 of one of the mold holes 4, and each second tube 82 fits in a first tube 81, and comprises a central through hole.

The top portion 41 of each mold hole 4 is suitable for housing at least part of the shoulder and pillar of a healing abutment or of an impression post, and for manufacturing the custom body of a healing abutment or of an impression post. The bottom portion of each mold hole is in turn suitable for housing the prosthetic connection of a healing abutment or the prosthetic connection of an impression post which are to be manufactured by these mold holes.

There are at least three different shapes of guide tabs, mold holes and tissue punch heads, each shape with at least three different sizes, each shape having a cross section which comprises at least one straight portion and one curved portion.

In the embodiment shown in this figure, there are three different shapes: triangular, square and rectangular. There are three available sizes for each shape: small, medium and large. These shapes and sizes try to correspond with the mean, high and low standard deviations of the dimensions available for the root trunks of different teeth incisors, canines, premolars and molars. This solution represents a compromise between providing standard shapes which may be also used in some other elements of the system and providing accurate shapes for creating emergence gingival profiles which adapt to the shapes of the different teeth.

This system is thus useful for performing several steps of a dental piece replacement. It provides the dentist with tools for creating the dental healing abutments and impression posts in a simple and accurate way, being able to adapt to a great amount of different patient situations.

Figures 2A, 2B, 2C:
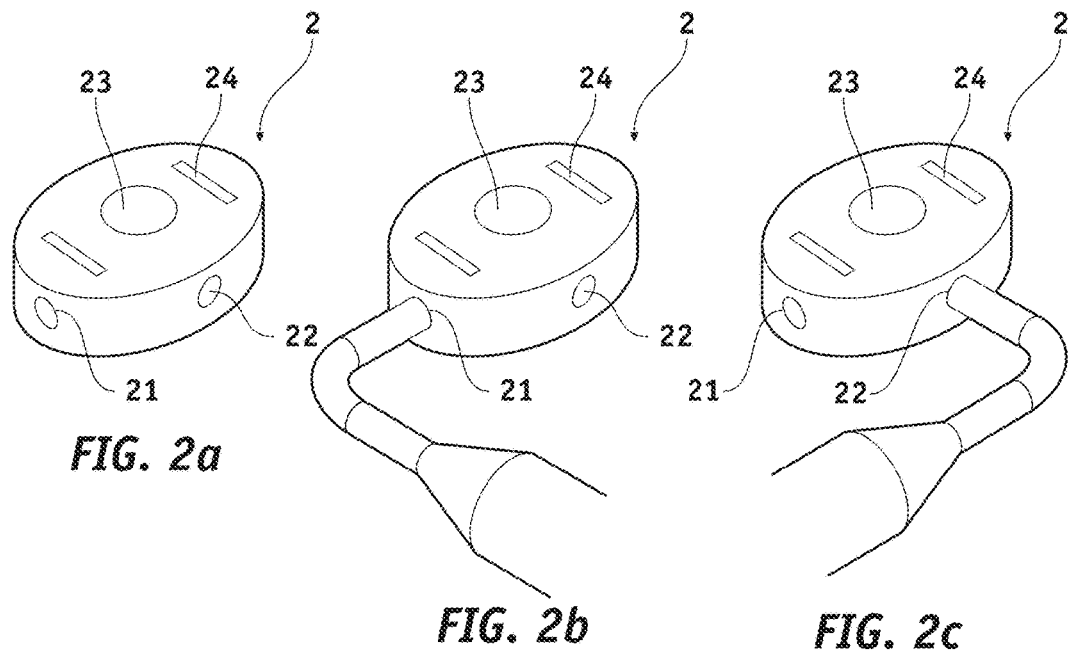
FIGS. 2a and 2c show details of guide tabs of particular embodiments of dental tools system according to the invention.

FIG. 2a shows an example of one of the guide tabs.

This guide tab 2 comprises a first lateral coupling recess 21 and a second lateral coupling recess 22, which is greater than the first lateral coupling recess 21. This guide tab 2 also comprises a central bore 23, suitable for letting a drilling tool pass through the guide tab 2. The central bore 23 is communicated with the second lateral coupling recess 22, but not with the first lateral coupling recess 21, because the second lateral coupling recess 22 is deeper than the first lateral coupling recess 21.

The first lateral coupling recess 21 is useful to introduce a first connecting pin of a handle 9, such as in FIG. 2b, but letting the central bore 23 free, in the event the dentist needs to use a drill tool across the guide tab 2, but needs to handle the guide tab 2 at the same time. The second lateral coupling recess 23 is useful to introduce a second connecting pin of a handle 9, bigger than the first connecting pin, such as in FIG. 2c. This is useful for a better handling of the guide tab 2, but as the second connecting pin introduced in the second lateral coupling recess may reach the central bore 23, this arrangement is not useful if the dentist needs to use the drill tool at the same time.

In other embodiments, the guide tab 2 has its first and second lateral coupling recesses substantially of the same shape, and further comprises a magnet, in at least one of these lateral recesses. In other embodiments, the magnet is comprised in the handle, and the guide tab is made of a ferromagnetic material. This ensures easy and quick engagement with a metallic handle. This guide tab also comprises the central bore, which is suitable for letting a drilling tool pass through the guide tab. As the engagement between the handle and the magnetic means does not require a great inner space from the lateral coupling recess, both first and second lateral coupling recesses are blind, none of them being in communication with the central bore. However, in some other embodiments, one of the lateral coupling recesses is not blind, and is in communication with the central bore, allowing a deeper introduction of the pin of the handle.

The guide tab comprises orientation marks 24, which are parallel and are suitable for helping the positioning of further dental tools.

Figure 3:
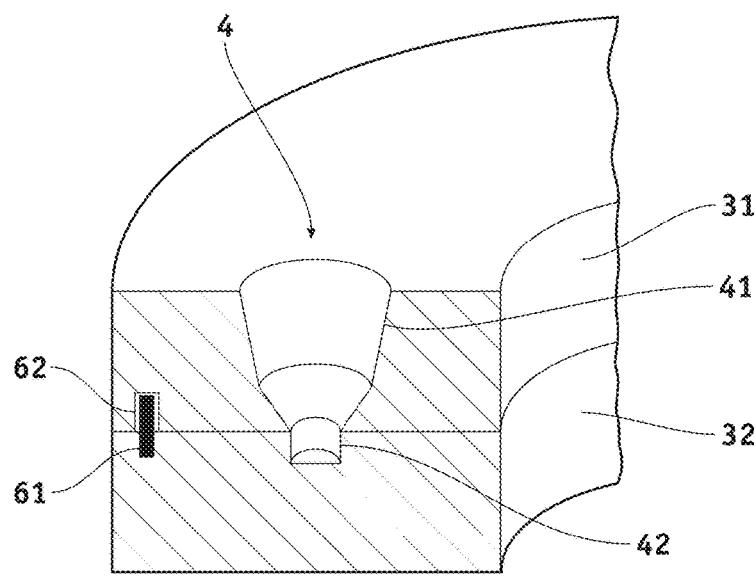
FIG. 3 shows a mold of a dental tools system according to the invention.
Figures 4A, 4B, 4C:
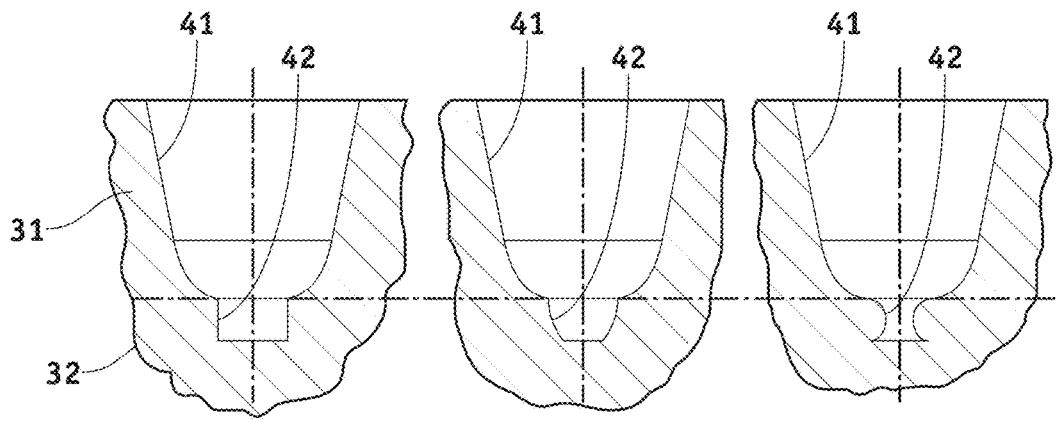
FIGS. 4a to 4f show mold views of different embodiments of dental tools system according to the invention.
Figures 4D, 4E, 4F:
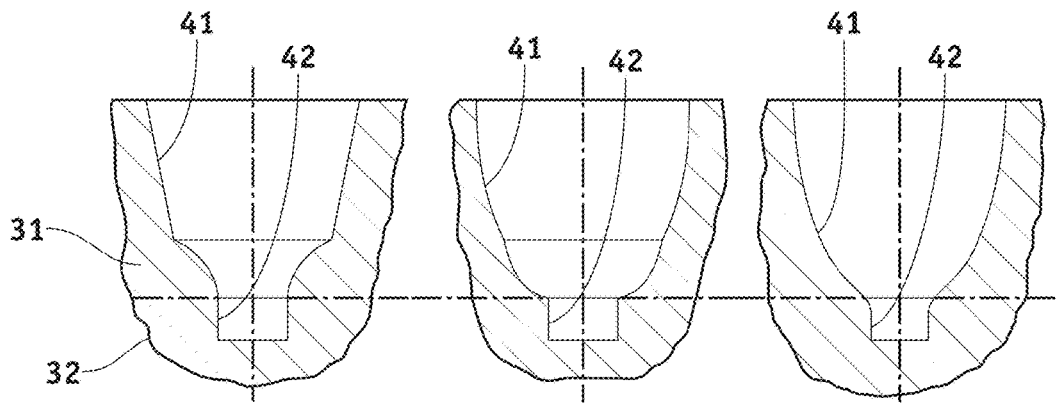

FIG. 3 shows a mold 3 of a dental tools system 1 according to the invention. This mold 3 comprises a mold base 32, which comprises the bottom portions 42 of the holes 4;

a mold superstructure 31, which comprises the top portions 41 of the mold holes 4, each top portion 41 having a cross section which decreases in the direction towards the mold base 32.

The mold base 32 and the mold superstructure 31 may be engaged in more than one operation position so that some top portions 41 match with different bottom portions 42 in each operation position.

The bottom portions 42 are intended to house the prosthetic connections of healing abutments and impression posts cores. The top portions 41 are in turn intended to house at least part of the shoulders and pillars of the healing abutments and impression posts cores, and to form the custom body of said healing abutments or impression posts. This housing can be achieved by means of snap on coupling and/or couple threading with, or without the use of a retention screw.

The top portions 41 have a cross section which varies in size and/or shape in the direction towards the mold base, but all cross sections are oriented according to parallel planes, which are perpendicular to the top straight direction. Some of the top portions have a cross section which comprises a straight portion and a curved portion. In particular embodiments, as shown in these figures, these cross sections are square with round edges, triangular with round edges or rectangular with round edges.

The mold base comprises first positioning means 61 and the mold superstructure comprises second positioning means 62 suitable for interacting with the first positioning means 61 in a stable position to keep constant the relative position of the mold base and the mold superstructure.

In some particular embodiments, these first and second positioning means are a vertical protrusion and a vertical groove, a ring and a seat, protrusions and notches, etc. First positioning means may be in the mold base and second positioning means may be in the mold superstructure or vice versa.

The first positioning means and the second positioning means have more than one stable position, so that the mold base and the mold superstructure may be securely attached in more than one position. This enables more combinations of top and bottom portions, thus enabling the existence of a wider range of holes. In some of the embodiments of the dental tools system, the base comprises a through opening so that if an object is introduced by this opening, it reaches the superstructure, and is able to separate it from the base by pushing.

In some embodiments, as shown in FIGS. 4a to 4f, the top portions 41 have inferior zones with cross sections which vary in size in the direction towards the mold base. In a side view, this may lead to a concave profile, a convex profile or a combination of them, as shown respectively in these FIGS. 4a to 4f. Further, in other embodiments, these cross sections of the inferior zones of the top portions may also change its shape with respect to the rest of the top portion.

The top portions have a regular surface, as that which may be expressed by a three-dimensional polynomic, exponential or logarithmic mathematical formula, or a combination thereof, with a mean roughness Ra lower than 10 μm.

Figure 5:
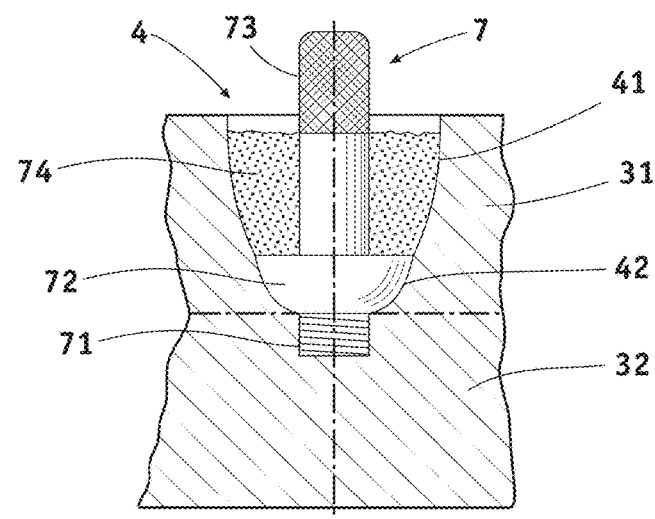
FIG. 5 shows the manufacturing of an abutment in a mold of the dental tools system according to the invention.

In some embodiments of the system, detachable inserts may be placed on the mold holes, to modify the final profile of some top and/or bottom portions. These detachable inserts may be made of silicone or any other imprintable substance, able to keep the shape by pressure. Due to the presence of these inserts, the molds may be able to produce dental healing abutments and impression posts in a wider range of shapes. These inserts can also be made out of metal, or plastic, or ceramic, or other suitable material A system according to the invention may be used when a patient needs the placement of an implant. When the dentist identifies the missing piece, he utilizes the set of guide tabs to find the guide tab which better suits the gap left by the missing piece. Once this guide tab is selected, the dentist will create a dental healing abutment, by placing an abutment core 7 in the mold hole which corresponds to the selected guide tab and pouring a biocompatible and curable material 74 on it, as shown in FIG. 5. The abutment core comprises a prosthetic connection 71, a shoulder 72 and a pillar 73, and is introduced in the mold hole 4, so that the prosthetic connection 71 is placed in the bottom portion 42 of the mold hole 4, while the shoulder 72 and the pillar 73 remain in the top portion 41. As the shoulder 72 fits with the inferior zone of the top portion 41, the biocompatible material 74 remains in the top portion 41 of the mold hole 4, without reaching the bottom portion 42, partially of fully covering the pillar 73.

When it is required, an impression post is created in the same mold hole that was used to manufacture the dental healing abutment. An impression post core is introduced instead, and biocompatible material is poured in the mold hole. The impression post core comprises a prosthetic connection, a shoulder and a pillar. The same as in the case of the healing abutment, the shoulder usually fits the inferior zone of the top portion of the mold hole, so that the biocompatible material remains in the top portion of the mold hole, partially covering the pillar.

If customized dental healing abutments and/or impression posts are to be manufactured with this mold, the inserts may be placed in a mold hole before the core is introduced.

These inserts are shaped by pressure or by any other means so that when they are located in the mold hole, the resulting profile is adequate for the patient's needs.

Figure 6:
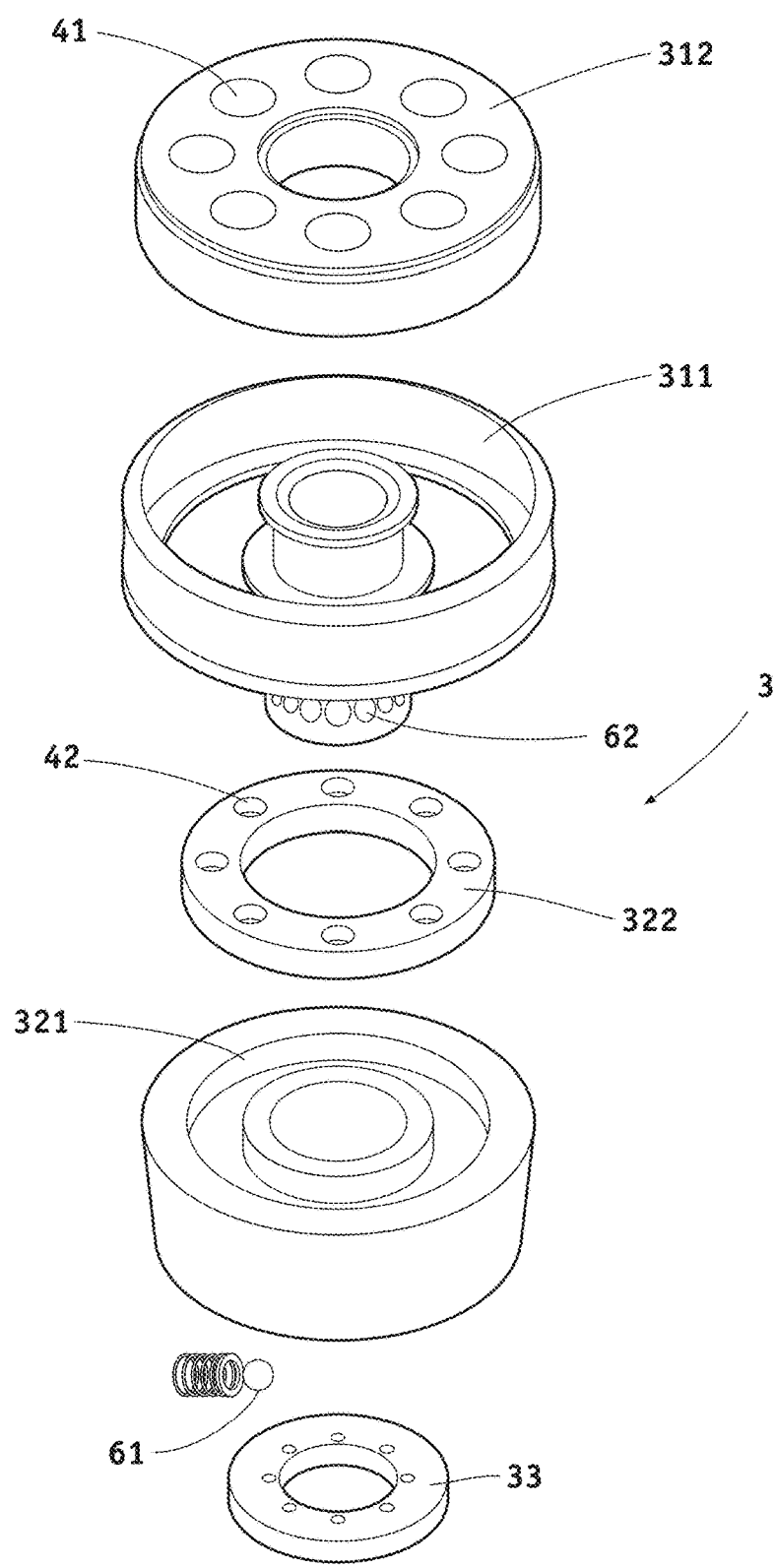
FIG. 6 shows an exploded view of a mold being part of a dental tools system according to the invention.
Figure 7:
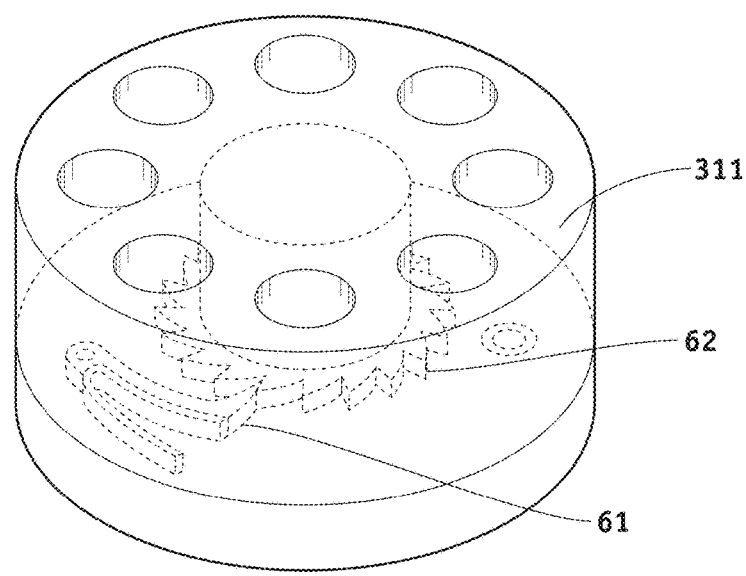
FIG. 7 shows a mold being part of an embodiment of a dental tools system according to the invention.
Figure 8:
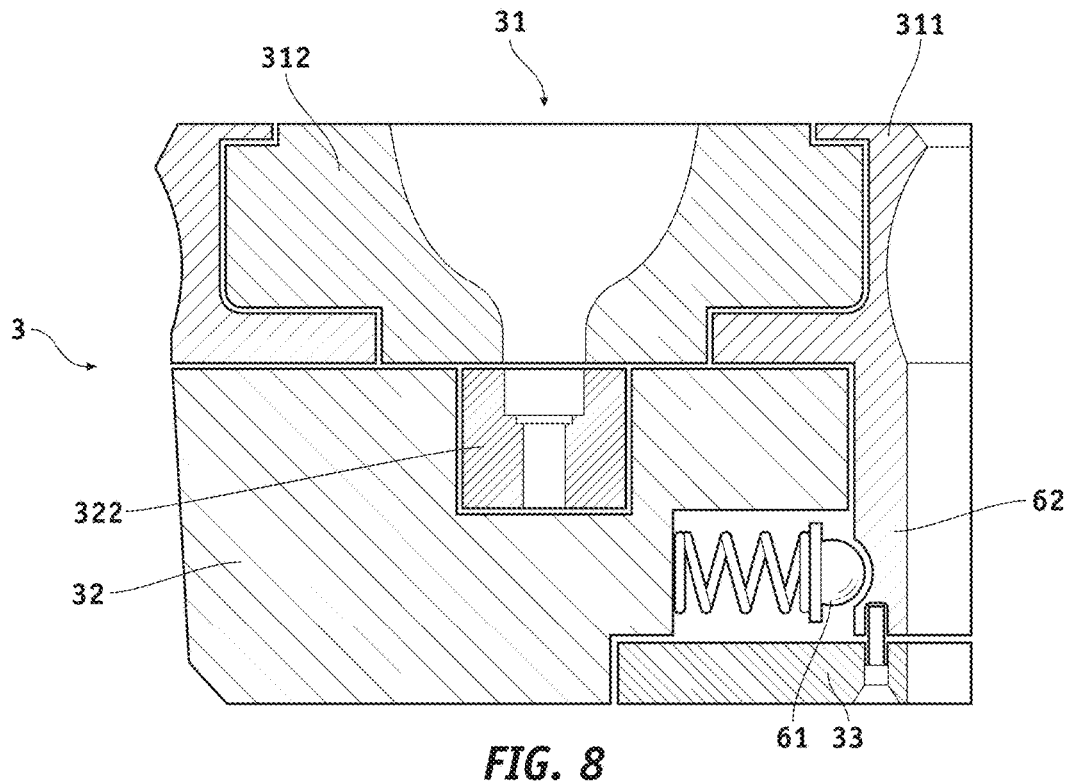
FIG. 8 shows a cross section of an embodiment of a mold of a dental tools system according to the invention.

FIGS. 6 to 8 show some particular features of different embodiments.

FIG. 6 shows an exploded view of a mold 3 being part of a dental tools system according to the invention. This mold 3 comprises a mold superstructure and a base but, in this case, the mold superstructure in turn comprises a first frame 311 and a first insert 312. The first insert 312 comprises the top portions 41 of the mold holes and is intended to be inserted inside the first frame 311.

In this figure, the mold base comprises a second frame 321 and a second insert 322. The second insert 322 comprises the bottom portions 42 of the mold holes and is inserted inside the second frame 321. The second frame 321 comprises first position means and the second insert 322 comprises second position means suitable for interacting with the first positioning means in a stable position to keep constant the relative position of the second frame 321 and the second insert 322. These means also allow the reproducible and reversible coupling of the second frame with the second insert. However, in different embodiments, the second frame 321 and the second insert 322 may be a single piece.

A cover 33 is also comprised in this mold 3, to avoid that the ball with a spring may exit the mold 3.

In the embodiment shown in this figure, the second positioning means are located in the first frame 311, and comprise a plurality of concavities 62. The first positioning means 61 are located in the second frame 321. In this figure, these first positioning means comprise a ball with spring. In different embodiments, this ball with a spring may be replaced just by a convex protrusion. In other embodiments, such as the one shown in FIG. 7, the concavities 62 of the first frame 311 are different, and the first positioning means 61 comprise a plate which may fit in each one of these concavities, as in the case of a roulette.

FIG. 8 shows a cross section of a mold 3 of a dental tool systems according to the invention. In this mold 3, the superstructure 31 comprises a first frame 311 and a first insert 312, but the base 32 is a single part. The first frame 311 comprises the second positioning means 62, which is a cavity. The first positioning means 61, which are comprised in the base 32, are a ball with a spring. The mold 3 further comprises a cover 33.

Figure 9:
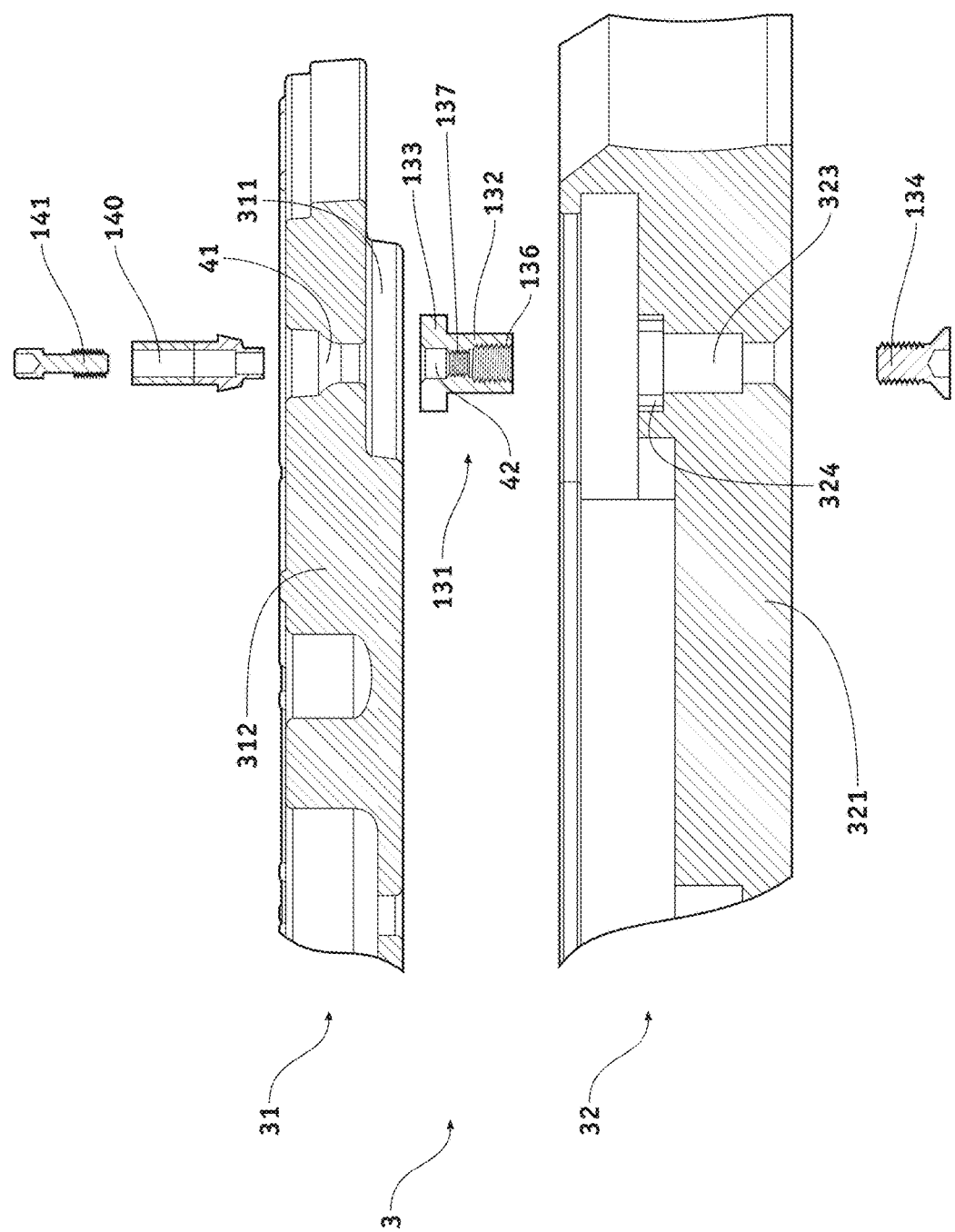
FIGS. 9 to 11 show some particular embodiments of the invention, regarding the inclusion of individual fitting inserts.
Figure 10:
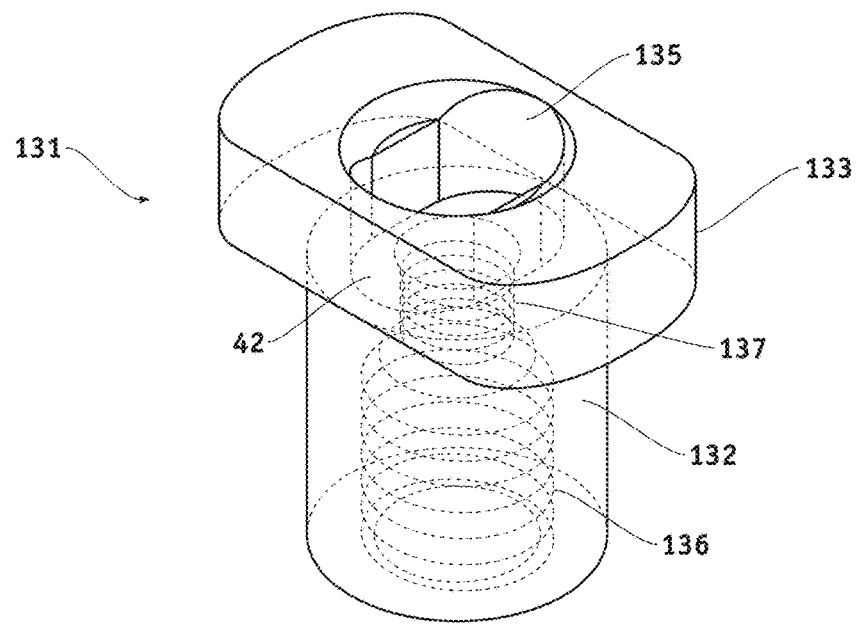
Figure 11:
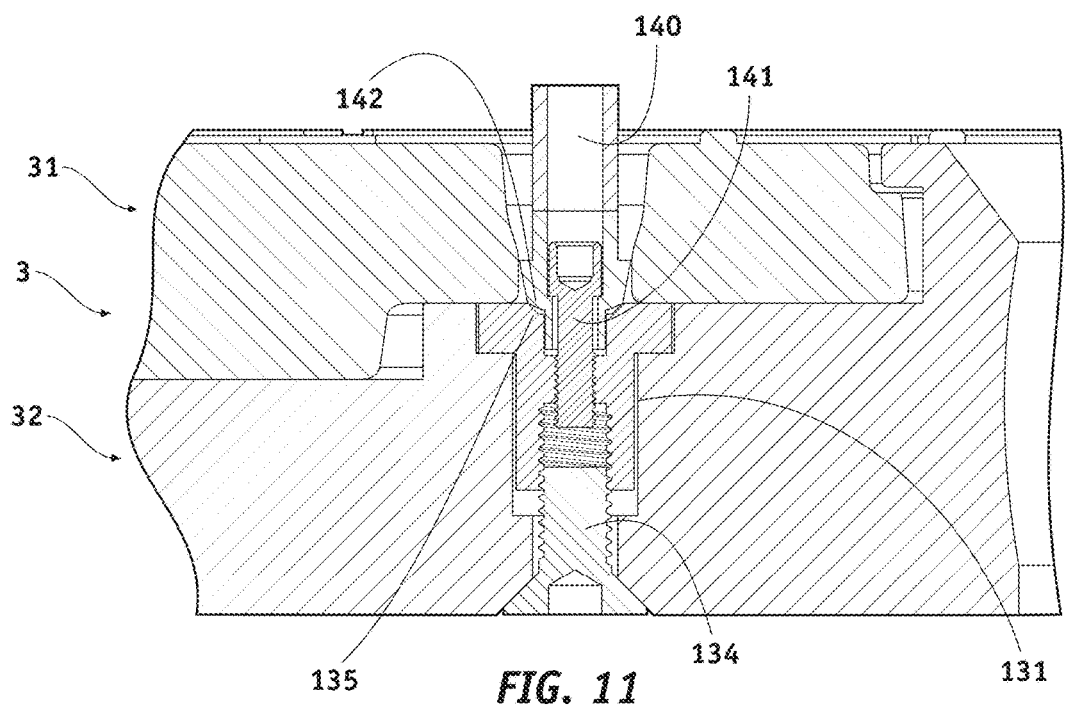

FIGS. 9 to 11 show some particular embodiments of the invention, regarding the inclusion of individual fitting inserts.

FIG. 9 shows an exploded view of a mold 3 included in an embodiment of the invention. This mold 3 comprises a mold superstructure 31 and a mold base 32.

The mold superstructure 31 comprises a first frame 311 and a first insert 312, the first insert 312 comprising the top portions 41 of the mold holes and being inserted inside the first frame 311.

The mold base 32 comprises in turn a second frame 321 with insert holes 323, each insert hole 323 comprising a seat 324. Further, it comprises a plurality of individual fitting inserts 131, each one of these individual fitting inserts 131 being adapted to fit in at least one of the insert holes 323 of the second frame 321. These individual fitting inserts 131 have an exterior shape, which is intended to fit inside one of the insert holes 323 of the mold base 32, and an interior shape, which is intended to act as a bottom portion 42. In this embodiment, all the insert holes 323 have the same shape, so the exterior shape of each insert is suitable for fitting in all the insert holes 323. This feature ensures versatility and easiness of use.

Each individual fitting insert 131 comprises a body 132 and a wing 133. The body 132 comprises one of the bottom portions 42, and the wing 133 is adapted to fit in the seat 324 of one of the insert holes 323, in such a way that the shape of the seat 324 prevents the individual fitting insert 131 from rotating once the individual fitting insert is fitted into the seat.

As may be seen in this figure, each individual fitting insert 131 is secured to the second frame 321 by means of a retention screw 134. The retention screw 134 fits with a lower threaded portion 136 of the individual fitting insert 131.

A healing abutment 140 is attached to the individual fitting insert 131 by means of an abutment screw 141, which couples to an upper threaded portion 137 of the individual fitting insert 131.

FIG. 10 shows a detail of an individual fitting insert 131 contained in an embodiment of the invention. As stated before, this individual fitting insert 131 comprises a body 132 and a wing 133. The individual fitting insert 131 further comprises a shoulder cavity 135, which is adapted to receive at least part of a prosthetic connection and/or a shoulder of a healing abutment. When the prosthetic connection and/or shoulder of a healing abutment fits this shoulder cavity 135, it cannot rotate, since the shape of the shoulder cavity 135 has not circular symmetry. The individual fitting insert 131 further comprises a lower threaded portion 136 and an upper threaded portion 137. The lower threaded portion 136 is intended to cooperate with the retention screw 134 which attaches the individual fitting insert 131 to the mold base 32. The upper threaded portion 137 is intended to couple with the abutment screw 141, which attaches the healing abutment to the individual fitting insert 131.

FIG. 11 shows an assembled view of the mold 3 of FIG. 9, with the mold superstructure 31 and the mold base 32, when a healing abutment 140 is arranged in it, and secured to the mold 3 by means of the abutment screw 141. The shoulder 142 of the healing abutment 140 rests partially on the shoulder cavity 135 of the individual fitting insert 131. The individual fitting insert 131 is in turn attached to the mold base 32 by means of the retention screw 134.

Additional Example 1

Figure 12:
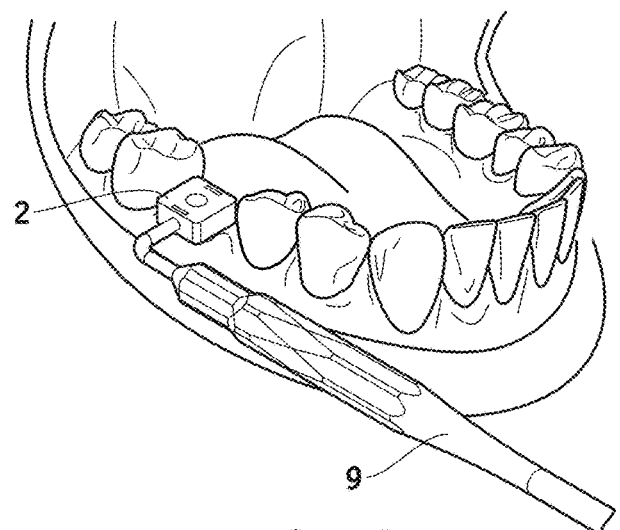
FIGS. 12 to 16 show steps of an example of method according to the invention.
Figure 13A:
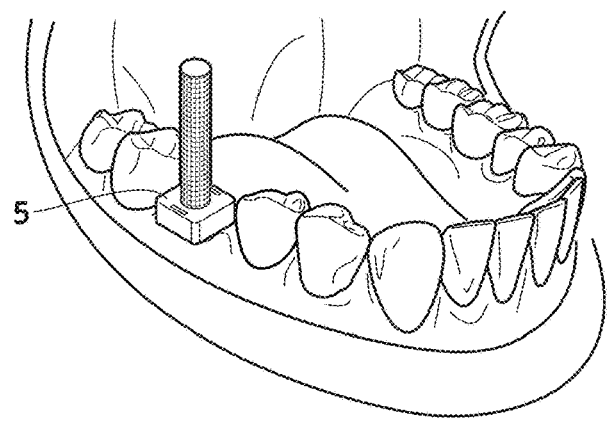
Figure 13B:
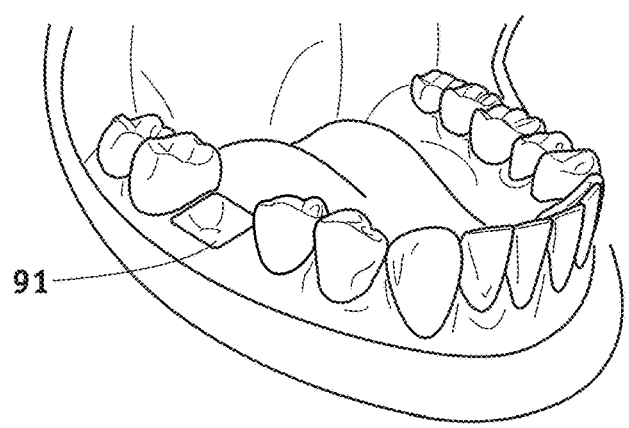

In a first example, a molar is missing and needs to be replaced by an implant. The dentist will utilize the handle 9 with a guide tab 2 that has a shape that corresponds to the shape of root trunk of a molar, that shape being square or rectangular. Based on the shape and size of the edentulous space of this particular patient he will select a guide tab that is of appropriate size and shape, e.g. the guide tab of the guide that corresponds to the square shape and medium size will be used initially for evaluation. If the guide tab does not fit properly in the edentulous space then he can switch to the smaller or larger size and even to the rectangular shape tab until he determines the appropriate tab of guide that best fits the shape and size of the edentulous space. For this example, a medium size square guide tab 2 is proper FIG. 12. Following, he utilizes the corresponding tissue punch head 5, which is the medium size square tissue punch head, and couples it in the handle of the tissue punch. Following the same positioning and orientation as per the use of the tab of the guide in the edentulous space information depicted by the orientation lines present on the top surface of the tab, he proceeds with the cut and removal of the gum tissue by pressure FIG. 13*a*, generating an emergence profile 91 of square shape and medium size as this was depicted initially by the guide FIG. 13*b*. Following, the dentist positions the guide tab 2 again in the edentulous space, aligning the guide tab 2 with the gingival emergence profile which has been generated by the tissue punch.

Figure 14:
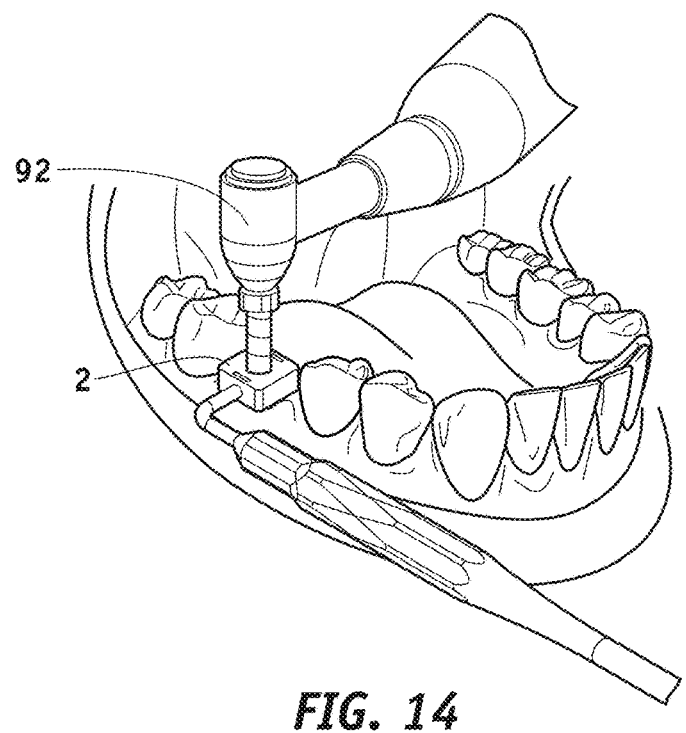
Figure 15:
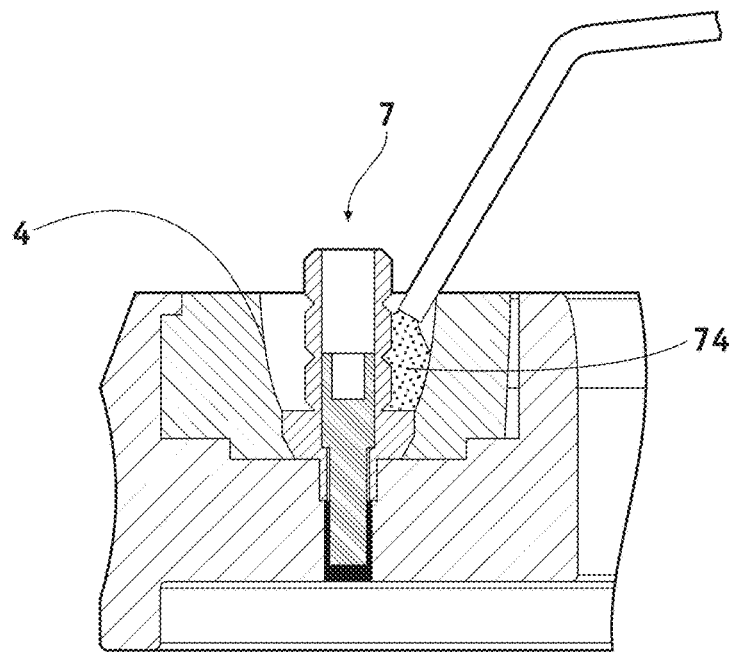

Then, he proceeds with marking of the initiation point of the osteotomy through the central bore of the guide tab by using a drilling tool 92 through the aforementioned central bore of the guide tab 2 (FIG. 14). This will ensure that the implant osteotomy will be properly placed generally at the center of the gingival emergence profile which has been generated by the tissue punch. Following, he completes the osteotomy and places an implant in the jaw, orienting at least one flat surface of its prosthetic connection to the same direction as per the orientation lines of the tab of the guide. Following, he installs an abutment core 7 in the mold hole 4 that has a top portion with the corresponding square shape and medium size and introduces a biocompatible material 74 into the open space of the top portion FIG. 15. After the material is cured and set, the dentist removes the square, medium size custom healing abutment, he disinfects it and couples it with the implant, to establish and maintain the generated gingival emergence profile.

Figure 16:
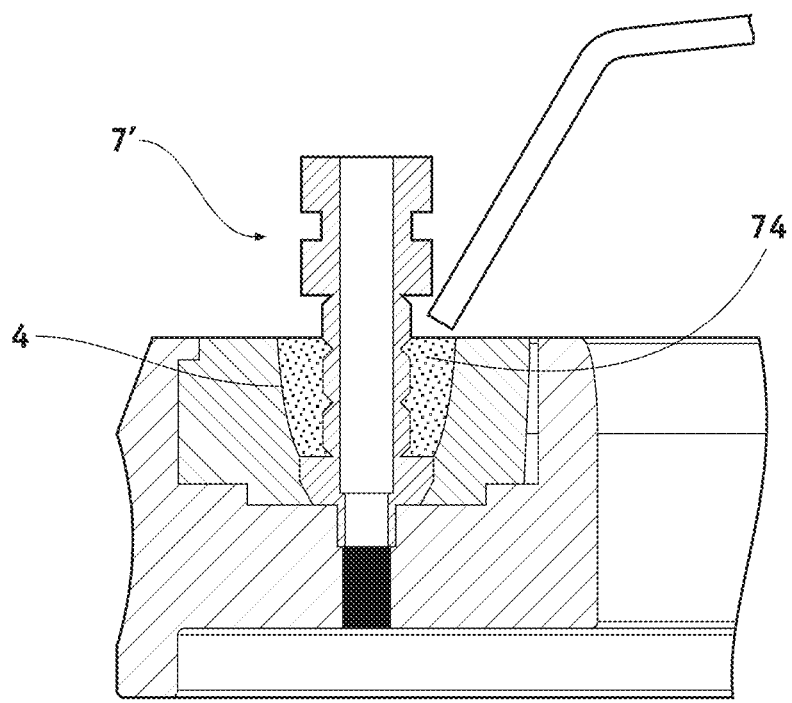

Following, or at a later stage when the osseointegration process is completed, the dentist installs into the same mold hole rectangular, medium size an impression post core 7' with the same shape and size prosthetic connection and shoulder as per the healing abutment core that was used before, and follows the same steps as per the custom healing abutment fabrication FIG. 16, thus manufacturing a custom shaped impression post that has a prosthetic connection and shoulder and also a custom body of the same shape and same size square, medium as the custom healing abutment present in the mouth. Thus, at least the sub-gingival portion of this custom impression post is an exact duplicate of the utilized custom healing abutment. He then uncouples the custom healing abutment from the implant and couples the custom impression post with the latter and takes an implant impression. The impression generated has recorded the accurate information of the established gingival emergence profile bottom portion: abutment shoulder and top portion: medium size and square shape and this can now be transferred on the working cast by introducing silicone mask material around the impression post that is present in the impression and subsequently pouring stone into the impression. This working cast has now the accurate information of the emergence profile generated and established in the mouth and it will be used by the lab technician to fabricate a final implant crown having an emergence profile similar to the one of the gingival, meaning a bottom portion of titanium or zirconia shoulder of the same shape and dimensions as per the healing abutment's and impression's post and a top portion of square and medium size shape as it was originally depicted as the most appropriate for this edentulous space by the guide tab, generated by the tissue punch, established by the custom healing abutment and recorded by the custom impression post.

Additional Example 2

Figure 17:
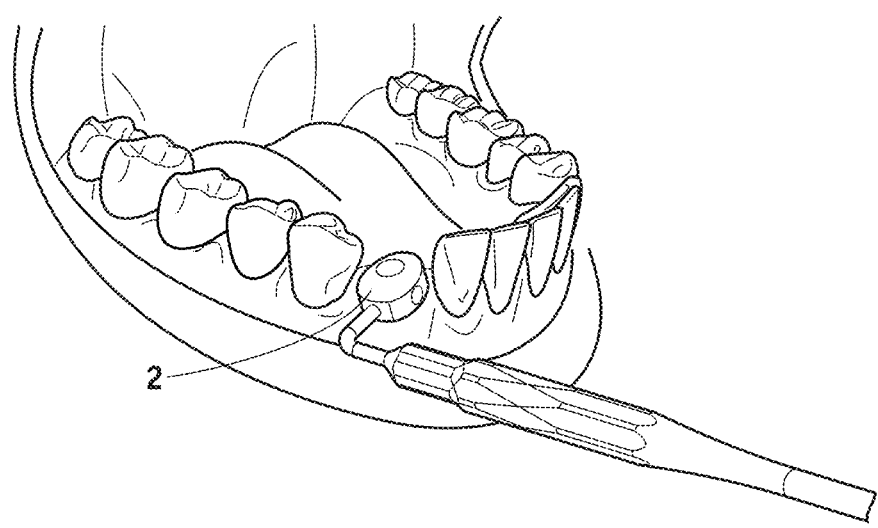
FIGS. 17 to 19 show some steps of an example of method according to the invention.

In a second example a patient is missing a lower canine anterior tooth and wants to have this missing tooth replaced with an implant. The dentist will utilize a guide tab 2 with triangular shape to evaluate the edentulous space FIG. 17. Thus, he will evaluate the space with the guide until he determines the proper size triangular shaped tab that fits better. For this example, a triangular shape of medium size tab is determined as the most appropriate. Thus, the emergence profile to be generated must have a top part with a triangular shape and medium size. The dentist positions a first accessory tube 81 that has a triangular shape and medium size in the edentulous space with orientation similar as the one depicted by the guide. Following he uses a curable moldable material to stabilize the tube in place, and uses the tissue punch with a tissue punch head of triangular shape and medium size to cut and remove the tissue through this first accessory tube and generate this way the desired gingival emergence profile.

Figure 18:
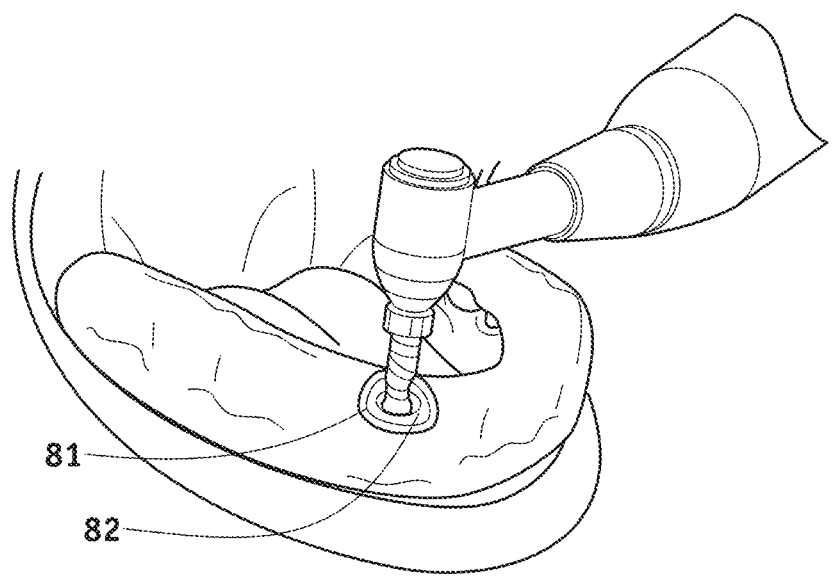
Figure 19:
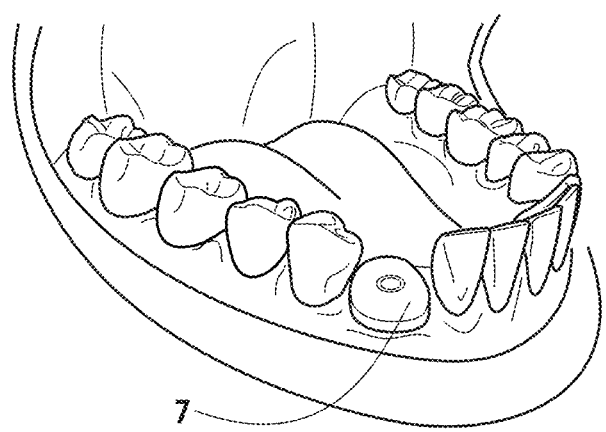
Figure 20A:
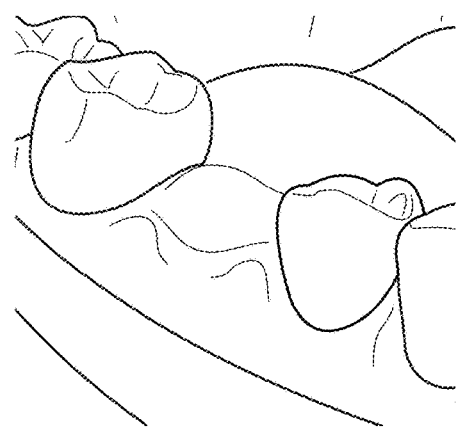
FIGS. 20a to 20b and 21a to 21c show an additional example of a method according to the invention.
Figure 20B:
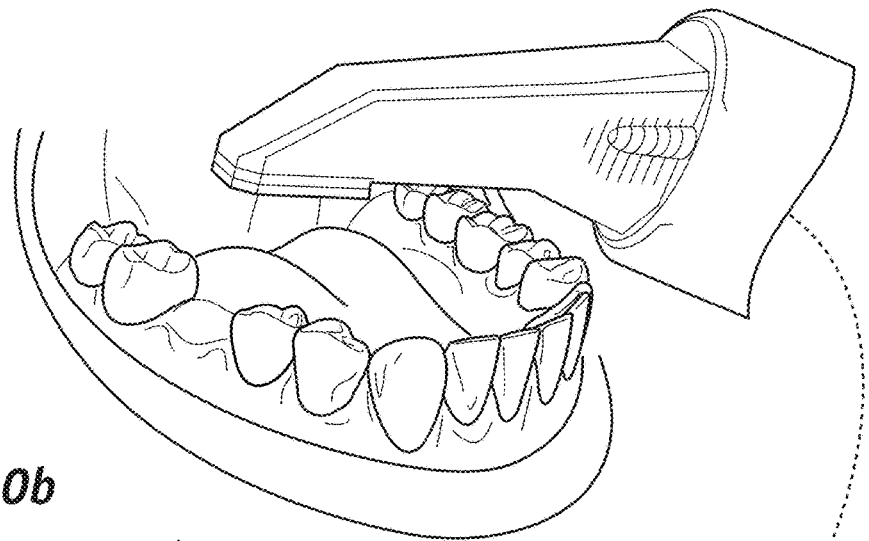
Figure 20B:
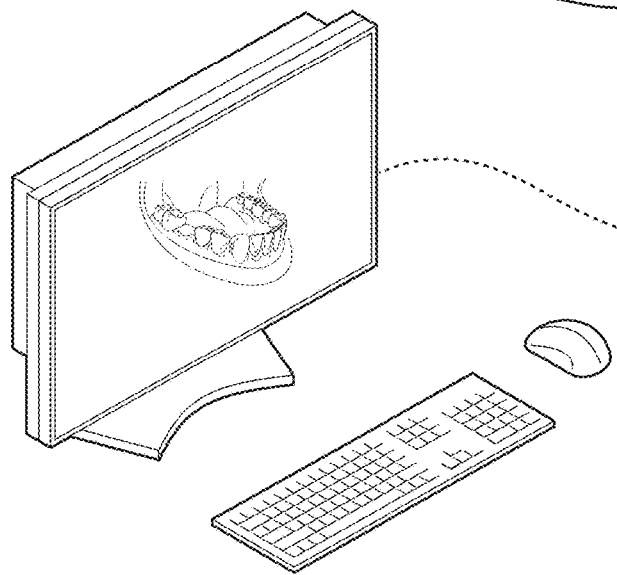
Figure 21A:
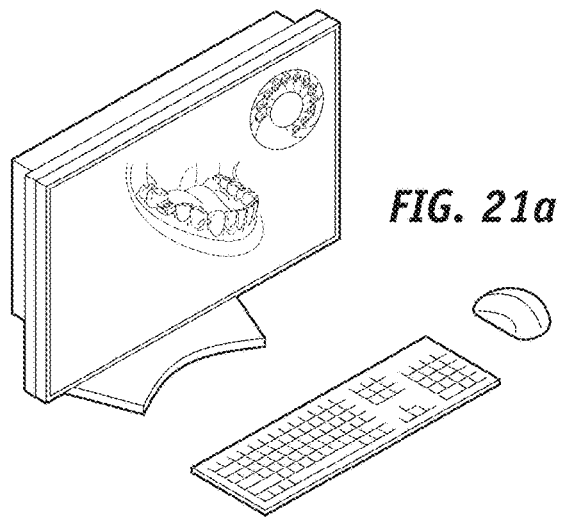
Figure 21B:
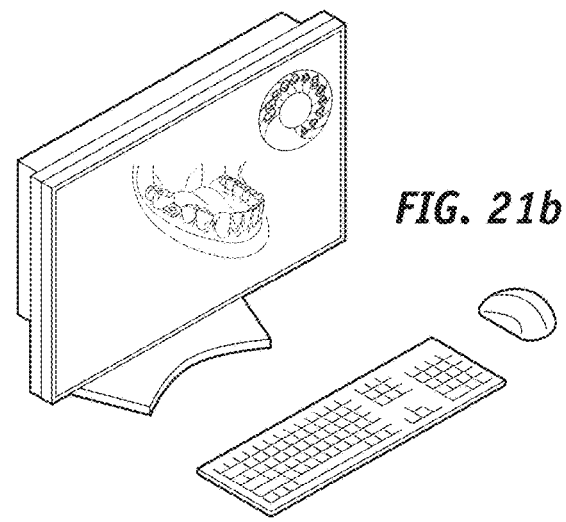
Figure 21C:
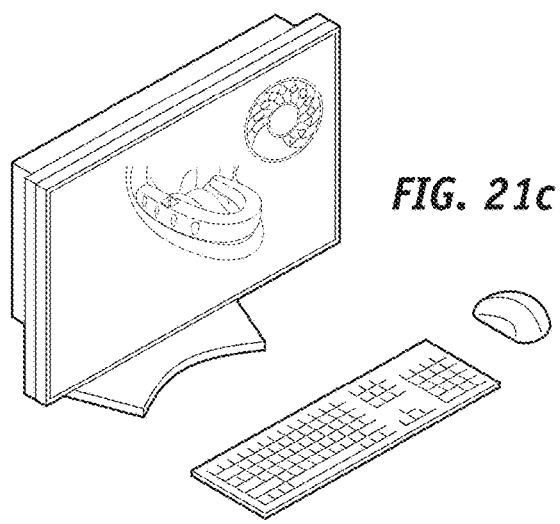

Following, the dentist couples the second accessory tube 82 to the first tube 81 and proceeds with the implant osteotomy by a drilling tool FIG. 18, and places the implant. Following, he fabricates a custom healing abutment and subsequently custom impression post with the same prosthetic connection and shoulder within the corresponding mold hole, that with triangular shape and medium size. These two elements now have the same prosthetic connection, shoulder and custom body triangular, medium size. Following, he couples the generated triangular, medium size, healing abutment 7 on the implant in order to establish and maintain the generated gingival emergence profile FIG. 19. At a later stage after the emergence profile has been established the dentist uncouples the healing abutment and couples with the implant the fabricated triangular medium size impression post and takes the impression. The rest of the steps as per the working cast and final crown fabrication are similar to the ones described on the first example.

Additional Example 3

In a third example, shown in FIGS. 20*a*-20*b* and 21*a*-21*c*, the dentist scans the edentulous space and the adjacent teeth with a digital scanner. Following, in a computer, the dentist selects from a digital library that is part of the software of the scanner and represents virtually the tabs of the guide, a virtual tab of the guide that best suits to the edentulous space of interest in order to select the appropriate emergence profile and subsequently the rest of the tools of the system that he will use. This virtual tab is the exact representation of the actual tab of the guide FIG. 18a, but since it is virtual, it can also be the exact negative representation of the actual tab of the guide FIG. 18b, serving this way the same purpose but making the virtual representation on the computer screen easier. Following, he utilizes this information code of virtual tab for the selection of the tissue punch head, of the first and second accessory tubes and of the top hole of the mold of the system, that he will use for performing all the stages of implant placement in relation to the virtual tab, following the same exact steps as per the methodology used with the actual tabs of the guide of the system. Specifically, at the stage of surgical implant placement, he will chose to use the head of the tissue punch with the corresponding code corresponding size and shape and/or the first and second tubes with corresponding code corresponding size and shape which tubes can be used with a surgical stent fabricated intra-orally or extra-orally with CAD-CAM technology FIG. 18c, but also the healing abutment and impression post that he will fabricate from the hole of the mold with the corresponding code corresponding size and shape. Moreover, the dentist has the ability before he utilizes the fabricated healing abutment and impression post to further introduce them in a CAD-CAM machine and further modify their custom body on their supra-gingival portion only, so that the methodology of use the system head of tissue punch, accessory tubes and hole of the mold is not affected since all of the tools of the system need to be inter-correlated at least on their portion that relates to the sub-gingival portion of the edentulous space that will receive the dental implant only. Since, the invention aims to solve a problem related to the sub-gingival portion of the edentulous space, any modifications in a CAD-CAM machinery of the supra-gingival portion only of the healing abutments and impression posts fabricated by the mold can facilitate the application of the system in further stages of the prosthetic treatment without expanding or changing the subject of the invention.

In this text, the term "comprises" and its derivations such as "comprising", etc. should not be understood in an excluding sense, that is, these terms should not be interpreted as excluding the possibility that what is described and defined may include further elements, steps, etc.

The invention is obviously not limited to the specific embodiments described herein, but also encompasses any variations that may be considered by any person skilled in the art for example, as regards the choice of materials, dimensions, components, configuration, etc., within the general scope of the invention as defined in the claims.

The invention claimed is:

1. Dental tools system comprising
a mold comprising a plurality of mold holes, each mold hole comprising a top portion and a bottom portion;
wherein the mold comprises
a mold base, which comprises the bottom portions of the mold holes;
a mold superstructure, which comprises the top portions of the mold holes, each top portion having a cross section which decreases in the direction towards the mold base;
wherein the mold base and the mold superstructure may be engaged in more than one operation position so that some top portions match with bottom portions in each operation position;
wherein the mold base comprises first positioning means and the mold superstructure comprises second positioning means suitable for interacting with the first positioning means in a stable position to keep constant the relative position of the mold base and the mold superstructure
wherein the first positioning means and the second positioning means have more than one stable position;
wherein the dental tools system further comprises:
a plurality of guide tabs; and
a plurality of tissue punch heads;
wherein
each guide tab fits in the top portion of one of the mold holes, the guide tab and the top portion of the mold hole having corresponding size and shape; and
each tissue punch head fits in the top portion of one of the mold holes, the tissue punch head and the top portion of the mold hole having corresponding size and shape;
wherein the fitting in the top portion is such that at least part of a top portion of the mold holes has a shape such that when a guide tab or a tissue punch head is placed in this top portion, it reaches a position with stable equilibrium.

2. The dental tools system according to claim 1, further comprising a plurality of first tubes and a plurality of second tubes, wherein each first tube fits in the top portion of one of the mold holes, and each second tube fits in a first tube, and comprises a central through hole.

3. The dental tools system according to claim 1, wherein there are at least three different shapes of guide tabs, mold holes and tissue punch heads, each shape with at least three different sizes, each shape having a cross section which comprises at least one straight portion and one curved portion.

4. The dental tools system according to claim 1, wherein at least one guide tab comprises a first lateral coupling recess and a second lateral coupling recess.

5. The dental tools system according to claim 4, wherein the second lateral coupling recess of the guide tab is greater than the first lateral coupling recess.

6. The dental tools system according to claim 4, further comprising a handle comprising first magnetic means and wherein the first and second lateral coupling recesses of the guide tab are substantially of the same shape, and wherein the first and/or second lateral coupling recesses comprise second magnetic means, adapted to interact with the first magnetic means.

7. The dental tools system according to claim 1, wherein at least one guide tab comprises a central bore, suitable for letting a drilling tool pass through the guide tab.

8. The dental tools system according to claim 1, wherein at least one guide tab comprises orientation marks, which are parallel and are suitable for helping the positioning of further dental tools.

9. The dental tools system according to claim 1, wherein the guide tabs are virtual and are included in a software which is suitable for evaluating the edentulous space of a patient and provide data to choose a mold hole and/or tissue punch head and/or first and second tubes.

10. The dental tools system according to claim 1 wherein the mold superstructure comprises a first frame and a first insert, the first insert comprising the top portions of the mold holes and being inserted inside the first frame; and the mold base comprises a second frame and a second insert, the second insert comprising the bottom portions of the mold holes and being inserted inside the second frame.

11. The dental tools system according to claim 10, wherein
the second positioning means are located in the first frame;
one of the first and second positioning means comprises a concavity; and
the other of the first and second positioning means comprises at least one of a ball with spring, a convexity or a plate.

12. The dental tools system according to claim 1, wherein
the mold superstructure comprises a first frame and a first insert, the first insert comprising the top portions of the mold holes and being inserted inside the first frame; and
the mold base comprises a second frame with insert holes, each insert hole comprising a seat;
the mold base further comprising a plurality of individual fitting inserts, each one of these individual fitting inserts being adapted to fit in at least one of the insert holes of the second frame,
each individual fitting insert comprises a body, comprising one of the bottom portions, and a wing, adapted to fit in the seat of one of the insert holes, in such a way that the shape of the seat prevents the individual fitting insert from rotating once the individual fitting insert is fitted into the seat.

13. The dental tools system according to claim 12, wherein each individual fitting insert is secured to the second frame by means of a retention screw.

14. The dental tools system according to claim 12, wherein the wing of at least one individual fitting insert comprises one shoulder cavity, adapted to receive at least part of a shoulder and/or prosthetic connection of a healing abutment.

15. The dental tools system according to claim 1, wherein some bottom portions are oriented in a different direction from some top portions.

16. The dental tools system according to claim 1, wherein the top portions have an inferior zone with a cross section which varies in size and/or shape in the direction towards the mold base, in such a way that the shape of the inferior zone of the top portion is different from the shape of the rest of the top portion.

17. The dental tools system according to claim 1, wherein some of the top portions (41) have at least one cross section which comprises a straight portion and a curved portion.

18. The dental tools system according to claim 1, wherein the top portions have a regular surface, as that which may be expressed by a polynomic, exponential or logarithmic mathematical formula, or a combination thereof, with a mean roughness Ra lower than 10 µm.

19. The dental tools system according to claim 1, further comprising detachable inserts suitable for modifying the final profile of some top and/or bottom portions.

* * * * *